(12) United States Patent
Siegel et al.

(10) Patent No.: US 8,361,016 B2
(45) Date of Patent: Jan. 29, 2013

(54) BALLOON CATHETER AND METHODS FOR PERICARDIOCENTESIS AND PERCUTANEOUS PERICARDIOTOMY

(75) Inventors: Robert James Siegel, Beverly Hills, CA (US); David Singh, San Francisco, CA (US); Bruce Addis, Redwood City, CA (US); Huai Luo, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 12/842,323

(22) Filed: Jul. 23, 2010

(65) Prior Publication Data

US 2011/0098672 A1 Apr. 28, 2011

Related U.S. Application Data

(63) Continuation-in-part of application No. PCT/US2009/031811, filed on Jan. 23, 2009.

(60) Provisional application No. 61/023,383, filed on Jan. 24, 2008.

(51) Int. Cl.
*A61M 29/00* (2006.01)
*A61M 31/00* (2006.01)

(52) U.S. Cl. .............. 604/103.07; 604/101.05

(58) Field of Classification Search .......... 604/101.01, 604/101.05, 103.06, 103.07
See application file for complete search history.

(56) References Cited

U.S. PATENT DOCUMENTS

| 4,575,371 A | 3/1986 | Nordqvist et al. |
| 4,921,478 A * | 5/1990 | Solano et al. ............ 604/509 |
| 5,195,507 A * | 3/1993 | Bilweis ................ 600/204 |
| 5,900,433 A | 5/1999 | Igo et al. |
| 6,117,105 A * | 9/2000 | Bresnaham et al. ....... 604/96.01 |
| 6,267,747 B1 * | 7/2001 | Samson et al. ........... 604/103.07 |
| 6,299,628 B1 * | 10/2001 | Harrison et al. ............... 606/194 |
| 6,692,458 B2 | 2/2004 | Forman et al. |
| 2001/0047163 A1 * | 11/2001 | Samson et al. ............... 604/509 |
| 2002/0013548 A1 | 1/2002 | Hinchliffe |
| 2002/0128598 A1 * | 9/2002 | Nobles ..................... 604/103.07 |
| 2004/0116868 A1 | 6/2004 | Forman et al. |
| 2006/0173441 A1 | 8/2006 | Gelfand et al. |
| 2007/0010708 A1 | 1/2007 | Ness |
| 2007/0142818 A1 | 6/2007 | Webler et al. |

OTHER PUBLICATIONS

ISR dated Mar. 6, 2009, PCT/US09/31811.
Written Opinion dated Mar. 6, 2009, PCT/US09/31811.
Toray USA, Inoue-Balloon Catheter descriptive webpage, http://www.torayusa.com/medical/ibpd.htm, downloaded Jul. 23, 2010.
Medtronic, Torqr Series Diagnostic Catheters descriptive webpage, http://www.medtronic.com/for-healthcare-professionals/products-therapies/cardiac-rhythm/ablation-products-for-arrhythmias/torqr-series/index.htm, downloaded Jul. 23, 2010.
Galli, M., et al. "Percutaneous balloon pericardiotomy for malignant pericardial tamponade," Chest, 1995; 108; 1499-1501.
Marcy, P.Y., et al. "Percutaneous treatment in patients presenting with malignant cardiac tamponade," Eur. Radiol. (2005) 15: 2000-2009.
Wang, H-J., et al. "Technical and prognostic outcomes of double-balloon pericardiotomy for large malignancy-related pericardial effusions," Chest, 2002; 122; 893-899.

(Continued)

*Primary Examiner* — Nicholas Lucchesi
*Assistant Examiner* — Aarti B Berdichevsky
(74) *Attorney, Agent, or Firm* — Hema Vakharia-Rao; Nixon Peabody LLP

(57) ABSTRACT

The present subject matter describes a balloon catheter and methods of using the balloon catheter. The balloon catheter is particularly useful for pericardiocentesis and percutaneous pericardiotomy.

27 Claims, 4 Drawing Sheets

OTHER PUBLICATIONS di Segni, E., et al. "Percutaneous balloon pericardiostomy for treatment of cardiac tamponade," European Heart Journal (1995) 16, 184-187.

Garcia del Barrio, L., et al. "Percutaneous balloon pericardial window for patients with symptomatic pericardial effusion," Cardiovasc. Intervent. Radiol. (2002) 24:360-364.

Law, D.A., et al. "Percutaneous balloon pericardiotomy: non-surgical treatment for patients with cardiac tamponade," The West Virginia Medical Journal, Nov./Dec. 1997, vol. 93; 310-312.

IPRP dated Aug. 5, 2010, PCT/US09/31811.

* cited by examiner

BALLOON CATHETER AND METHODS FOR PERICARDIOCENTESIS AND PERCUTANEOUS PERICARDIOTOMY

CROSS REFERENCE TO RELATED APPLICATIONS

This application is a continuation in part of International Application No. PCT/US2009/31811, filed Jan. 23, 2009, which designated the U.S. and that International Application was published under PCT Article 21(2) in English. This application also includes a claim of priority under 35 U.S.C. §119(e) to U.S. provisional patent application No. 61/023,383, filed on Jan. 24, 2008.

FIELD OF SUBJECT MATTER

This subject matter relates to the performance of pericardiocentesis and percutaneous creation of a pericardial window.

BACKGROUND OF THE SUBJECT MATTER

All publications herein are incorporated by reference to the same extent as if each individual publication or patent application was specifically and individually indicated to be incorporated by reference. The following description includes information that may be useful in understanding the present subject matter. It is not an admission that any of the information provided herein is prior art or relevant to the presently claimed subject matter, or that any publication specifically or implicitly referenced is prior art.

Pericardiocentesis is a procedure wherein the fluid in the pericardium is aspirated. Fluid aspiration is necessary to relieve the pressure on the heart or to analyze the fluid surrounding the heart. Examples of indications for pericardiocentesis include but are not limited to cardiac tamponade, pericarditis, and pericardial effusion. In instances wherein long term drainage is necessary, a cardiothoracic surgeon will create a pericardial window, in which an opening is made in the pericardium to drain the fluid. The procedure is known as a pericardiotomy or pericardiostomy.

Balloon dilation of the pericardium is currently performed with an aortic balloon valvuloplasty catheter. Percutaneous balloon pericardiotomy is a percutaneous procedure using a balloon catheter to produce a pericardial window, in effect, by tearing the pericardium in patients with pericardial effusion. The procedure is typically an alternative to conventional pericardiotomy to avoid surgery in patients with a poor prognosis. Percutaneous pericardiotomy procedures have been performed with a single or double balloon catheter. Generally, the procedure involves having the balloon span across the pericardium and quickly inflating the balloon to create the pericardial window and is performed under fluoroscopic guidance to ensure that the balloon spans across the pericardium and that a pericardial window is created.

Nonetheless, these procedures require fluoroscopic guidance and a highly skilled interventional cardiologist. Thus, there exists a need in the art for a device and a method for percutaneous pericardiotomy that does not require the fluoroscopic guidance and that may be more simple to perform.

BRIEF DESCRIPTION OF THE FIGURES

Exemplary embodiments are illustrated in referenced figures. It is intended that the embodiments and figures disclosed herein are to be considered illustrative rather than restrictive.

DETAILED DESCRIPTION OF THE SUBJECT MATTER

All references cited herein are incorporated by reference in their entirety as though fully set forth. Unless defined otherwise, technical and scientific terms used herein have the same meaning as commonly understood by one of ordinary skill in the art to which this subject matter belongs.

One skilled in the art will recognize many methods or materials similar or equivalent to those described herein, which could be used in the practice of the present subject matter. Indeed, the present subject matter is in no way limited to the methods or materials described.

The present subject matter relates to a balloon catheter and percutaneous methods of using the balloon catheter for pericardiocentesis and pericardiotomy. The inventive balloon catheter does not require guidance by fluoroscopy and allows for the creation of a pericardial window with standard pericardiocentesis techniques. Furthermore, the inventive catheter may remain in the pericardium after balloon dilatation for further drainage of fluid from the pericardial space.

One embodiment of the present subject matter is a tulip-shaped balloon catheter (although other shapes and configurations are within the scope of the present invention). The tulip-shaped balloon catheter comprises: a catheter and a first inflatable balloon attached to the catheter, wherein the first inflatable balloon has an axis and comprises a first section proximal to the user being generally conical along the axis, and a second section distal to the user being generally half-spherical along the axis.

In one embodiment, the length of the first section is shorter than the length of the second section. In another embodiment, the length of the first section is substantially equal to the length of the second section. In another embodiment, the length of the first section is longer than the length of the second section.

In various embodiments, the largest diameter of the first inflatable balloon is about 6 to 26 mm and the length of the first inflatable balloon is about 5 to 25 mm along the axis.

Figure 4A:
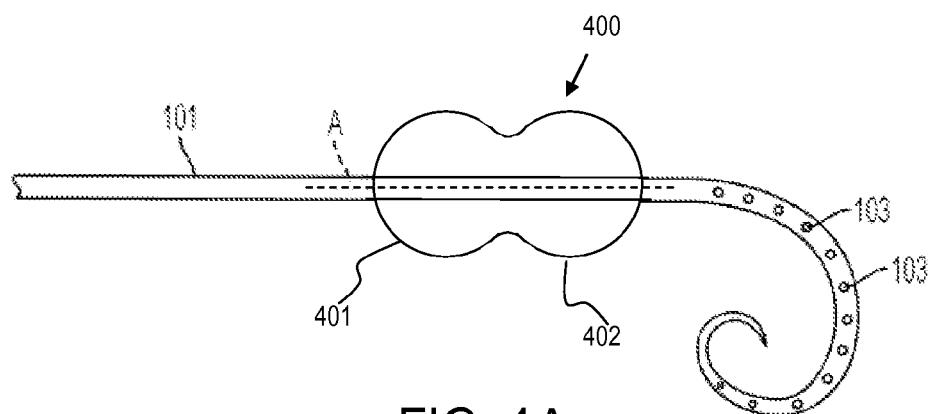
FIG. 4A depicts a two-sphere balloon catheter in accordance with an embodiment of the present subject matter.
Figure 4B:
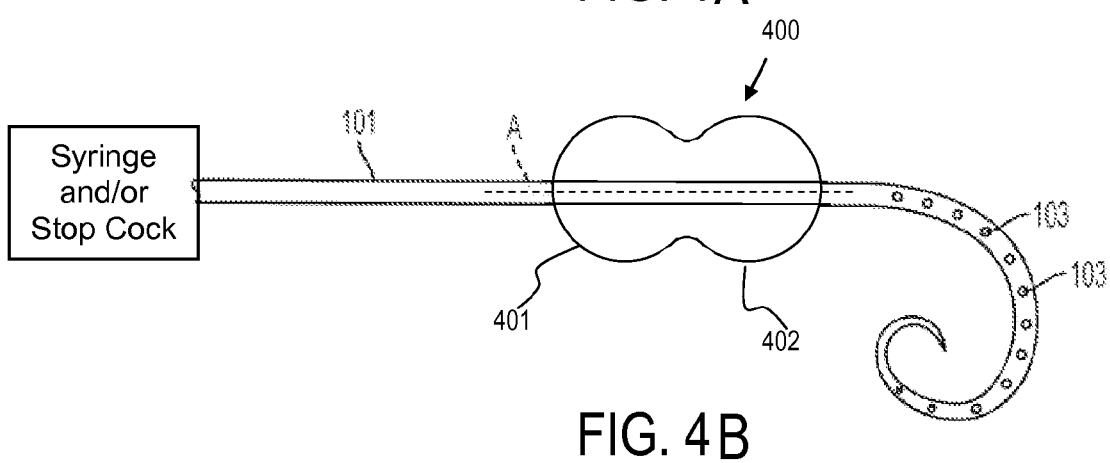
FIG. 4B depicts a two-sphere balloon catheter with a syringe and/or a stop cock in accordance with an embodiment of the present subject matter.

In an alternate embodiment (FIG. 4), the first inflatable balloon 400 has an axis and comprises a first section 401 proximal to the user being generally spherical along the axis, and a second section 402 distal to the user also being generally spherical along the axis. In an embodiment, this shape may mimic an Inoue balloon catheter (available from Toray International America Inc.). When used in operation, the second section may be dilated first, followed by the first section. The second section would then hold the catheter within the pericardium and the waist of the balloon may dilate the pericardium (or pericardial rim).

The catheters may be any size. One of skill in the art can readily determine sizes that are suitable for particular uses of the tulip-shaped balloon catheter. For pericardiocentesis or pericardiotomy in a human subject, catheter sizes 5 to 14 French, inclusive, may be particularly useful.

The catheters may also be any type that is suitable for insertion into a body cavity. For pericardiocentesis or pericardiotomy in a human subject, a pigtail catheter or a straight catheter may be particularly useful. The catheter may optionally comprise drainage holes to allow fluid in the pericardial space to be removed through the catheter.

In an embodiment, the catheter may be a braided catheter. This may render the catheter more torquable: that is, it may be easier to manipulate. Moreover, braiding may impart strength to a catheter, which may prevent it from tearing or fracturing during catheter withdrawal (non-braided catheters are more likely to stretch or even tear). Additional benefits of using a braided catheter may include, but are not limited to, Improved tracking of the catheter over a guidewire during catheter placement, enhanced catheter manipulation during catheter placement and catheter removal, improved safety due to, e.g., a reduced risk for catheter fracture or tearing during catheter removal, and marked enhancement of the visualization of the intra-pericardial catheter by ultrasound during the procedure and during follow-up (e.g., standard trans-thoracic 2D echo), as well as by chest X-ray (e.g., post procedure and during follow-up) and by fluoroscopy (during the procedure, if desired). Braided catheters are generally constructed by lining the catheter with an inner stainless steel mesh, and such catheters are commercially available. Such catheters are available, for instance, from Medtronic, Inc. under the trade name TORQR.

In an alternative embodiment, the tulip-shaped balloon catheter further comprises a second inflatable balloon adapted to secure and prevent the catheter from being pulled out of the pericardial space. The second inflatable balloon is distal to the first balloon. The second inflatable balloon may range in shape and size from being generally spherical to generally disk-shaped, where the length of the balloon along the axis is smaller than the diameter of the balloon. A range of additional shapes and configurations may be appropriate for the second inflatable balloon, so long as such shapes and configurations enable the second inflatable balloon to be used for securing and/or preventing the catheter from being pulled out of the pericardial space, as will be readily appreciated by those of skill in the art.

The first and the second inflatable balloons may be composed of any material that enables their inflation and deflation as well as materials compatible for medical use. Examples of suitable materials include but are in no way limited to poly-vinyl chloride (PVC), polyethylene terephthalate (PET), nylon, rubber, polyethylene and polyurethane.

The balloon catheter is configured for inflating and deflating the first and/or the second balloon. For example, the configuration may be similar to those of aortic balloon valvuloplasty catheters. In various embodiments, the tulip-shaped balloon catheter may comprise one or more inflation lumens and/or one or more deflation lumens that are in fluid communication with the first and/or the second inflatable balloon. A gas or liquid can be introduced from an external inflation device to inflate the first and/or the second inflatable balloon, or segmented portions thereof, such as in the case of the two-sphere balloon described above in which two spherical segments may be inflated simultaneously or independently of one another. The inflation device may also be used to withdraw the gas or liquid to deflate the first and/or the second balloon. Inflation devices can be any inflation device known in the art that is suitable for use for balloon catheters or dilation devices. In one embodiment, inflation of the tulip-shaped balloon catheter may be accomplished by utilizing a syringe configured to administer a pre-specified amount of air or fluid. The syringe is attached to the end of the catheter and depressed. This will force liquid or air through the catheter resulting in balloon inflation. The amount of air or fluid required for complete balloon inflation can be pre-determined such that a fixed volume can deployed each time. This technique will ensure that complete balloon inflation can be reliably and reproducibly performed. Further, a three-way stop cock can be utilized on the catheter to seal the inflated balloon.

Figure 1A:
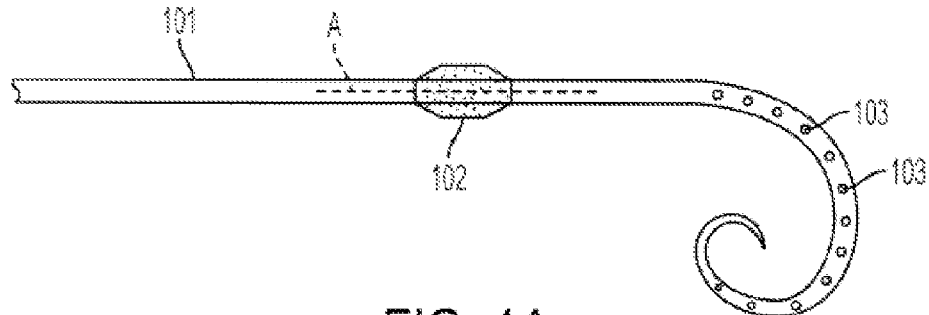
FIG. 1A depicts a deflated tulip-shaped balloon catheter in accordance with an embodiment of the present subject matter.
Figure 1B:
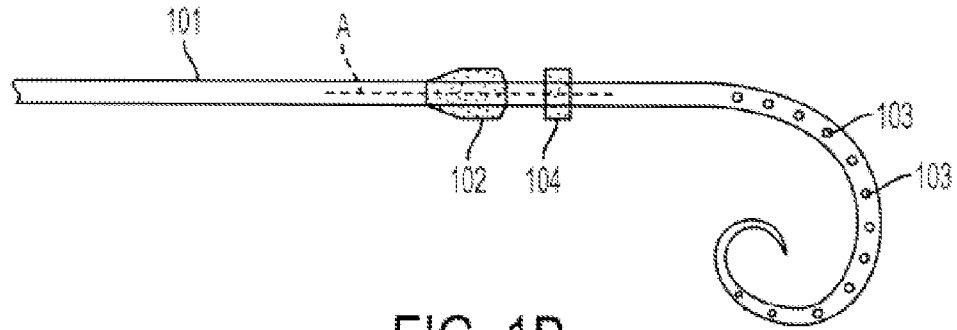
FIG. 1B depicts a deflated tulip-shaped balloon catheter with second balloon in accordance with an embodiment of the present subject matter.
Figure 1C:
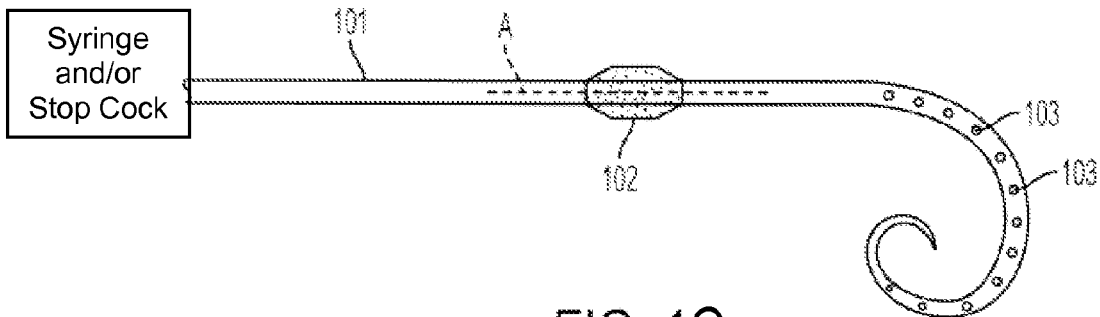
FIG. 1C depicts a deflated tulip-shaped balloon catheter with a syringe and/or a stop cock in accordance with an embodiment of the present subject matter.
Figure 1D:
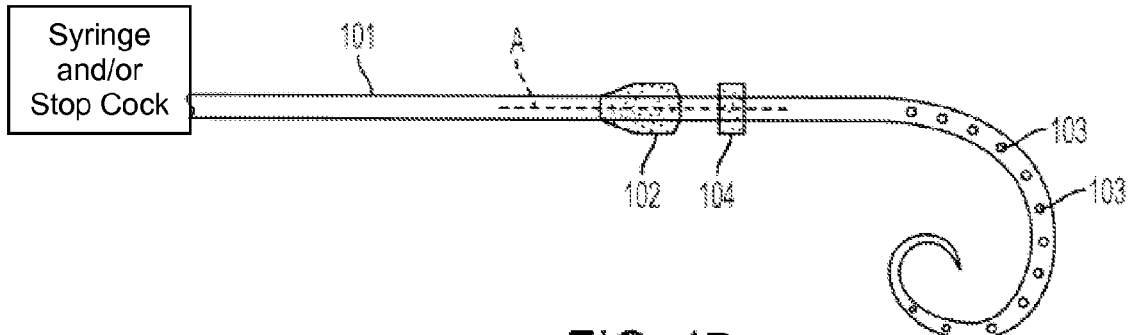
FIG. 1D depicts a deflated tulip-shaped balloon catheter with second balloon and with a syringe and/or a stop cock in accordance with an embodiment of the present subject matter.

As an example, FIG. 1A depicts a deflated tulip-shaped balloon catheter comprising a pigtail catheter 101, a tulip-shaped balloon in its deflated state 102 is along the axis A. Drainage holes 103 are also shown. FIG. 1B shows a deflated tulip-shaped balloon catheter comprising a pigtail catheter 101, a tulip-shaped balloon in its deflated state 102 and a second balloon in its deflated state 104. Drainage holes 103 are also shown.

Figure 2A:
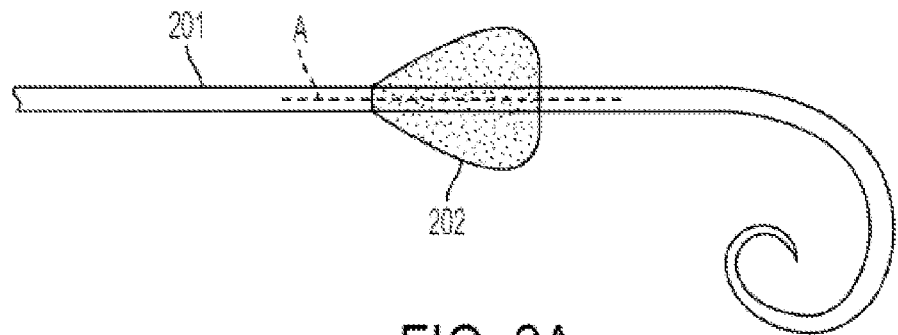
FIG. 2A depicts an inflated tulip-shaped balloon catheter in accordance with an embodiment of the present subject matter.
Figure 2B:
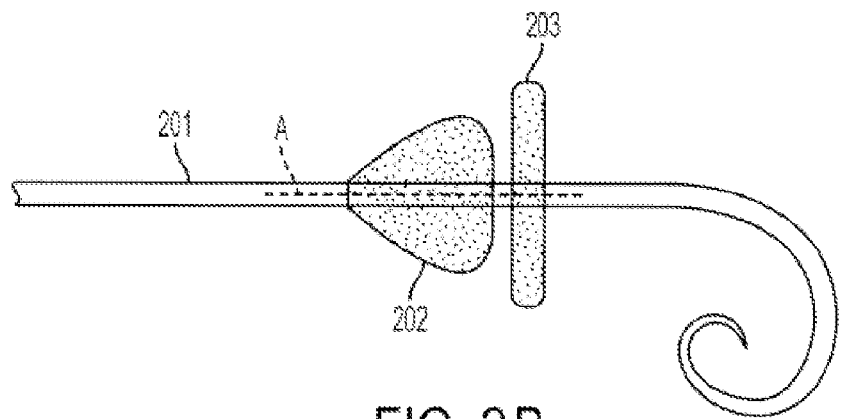
FIG. 2B depicts an inflated tulip-shaped balloon catheter with second balloon in accordance with an embodiment of the present subject matter.
Figure 2C:
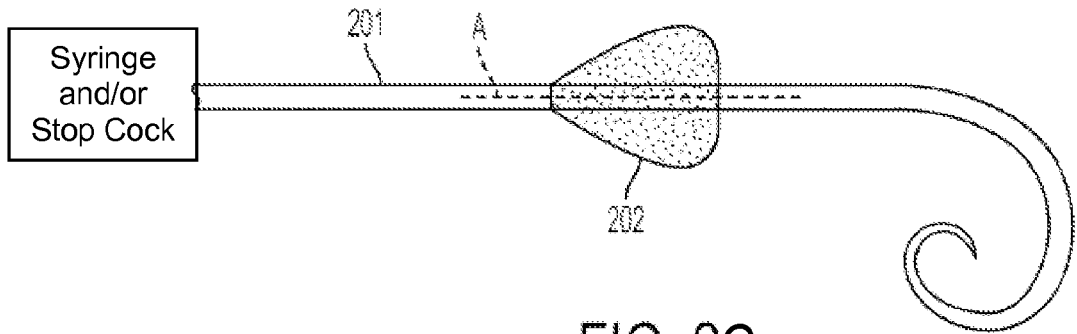
FIG. 2C depicts an inflated tulip-shaped balloon catheter with a syringe and/or a stop cock in accordance with an embodiment of the present subject matter.
Figure 2D:
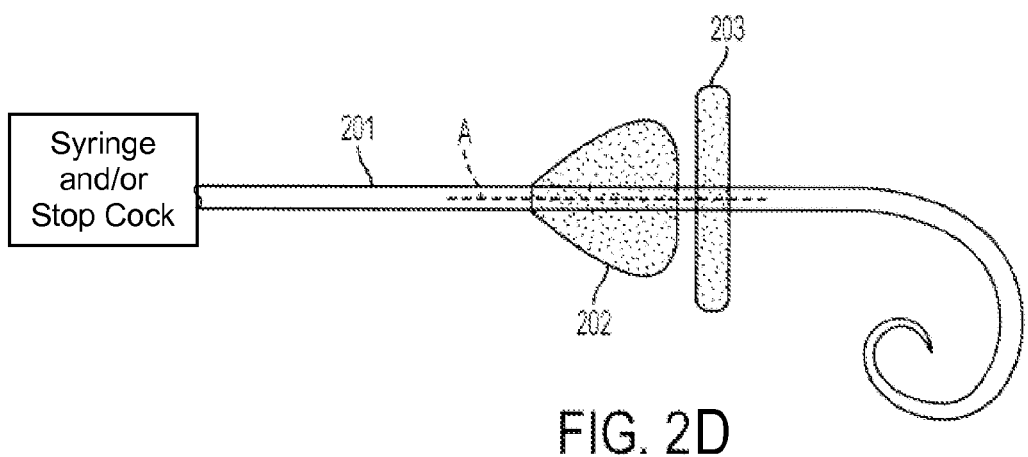
FIG. 2D depicts an inflated tulip-shaped balloon catheter with second balloon and with a syringe and/or a stop cock in accordance with an embodiment of the present subject matter.

As an example, FIG. 2A depicts an inflated tulip-shaped balloon catheter comprising a pigtail catheter 201, a tulip-shaped balloon in its inflated state 202. FIG. 2B shows an inflated tulip-shaped balloon catheter comprising a pigtail catheter 201, a tulip-shaped balloon in its inflated state 202 and a second balloon in its inflated state 203.

The balloon allows for various functions. First, the balloon can dilate a hole made in the pericardium. Second, the balloon can prevent the catheter from being pulled out of the pericardial space. This may be particularly beneficial when the balloon catheter is left in the pericardial space for prolonged drainage of the fluid from the pericardial space. Third, a medical practitioner can pull the tulip-shaped balloon with the balloon inflated to slowly increase the hole in the pericardium (essentially by tearing the pericardium). As such, a pericardial window is created without the need for surgery, or the use of fluoroscopy to determine the location of the catheter or the balloon or to determine whether a sufficient size hole in the pericardium is made.

Another embodiment of the present subject matter provides for a method of using the balloon catheter to perform pericardiocentesis. The method comprises: providing a balloon catheter as described herein; advancing the balloon catheter into the pericardial space; and draining fluid from the pericardial space of the subject. The fluid may be drained through the small hole that is created by the balloon catheter into the chest cavity. Alternatively, the fluid may be drained by the catheter by withdrawing the fluid through the catheter. For example, about 100 cc of fluid may be drained from the pericardial space. The method may also comprise inflating the balloon to prevent the balloon from being pulled out of the pericardial space. The method may further comprise deflating the balloon and removing the balloon catheter from the subject. Additionally, the method may comprise using ultrasound to verify that the balloon catheter is in the pericardial space.

In embodiments wherein the balloon catheter comprises a second balloon, the method may further comprise inflating the second balloon to secure and prevent the catheter from being pulled out of the pericardial space. The second balloon may be deflated prior to removal of the catheter from the subject Advancing the balloon catheter into the pericardial space may be performed by implementing the use of a guidewire, whereas the catheter passes over the guidewire and into the pericardial space. One of skill in the art will readily appreciate methods for implementing the use of a guidewire in the present subject matter for application in the pericardial space. For example, this may be performed by making an incision, inserting a hollow needle through the incision, advancing the hollow needle towards the pericardium and into the pericardial space, confirming that the hollow needle is in the pericardial space, passing a guidewire through the hollow needle into the pericardial space, and withdrawing the hollow needle. The catheter can now be passed over the guidewire into the pericardial space.

Figure 3A:
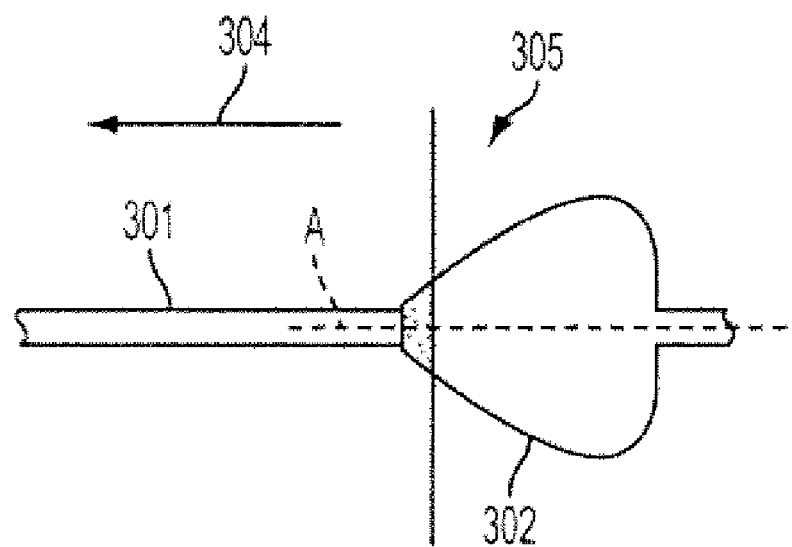
FIG. 3A depicts a tulip-shaped balloon catheter in a various stage of use in accordance with an embodiment of the present subject matter.
Figure 3B:
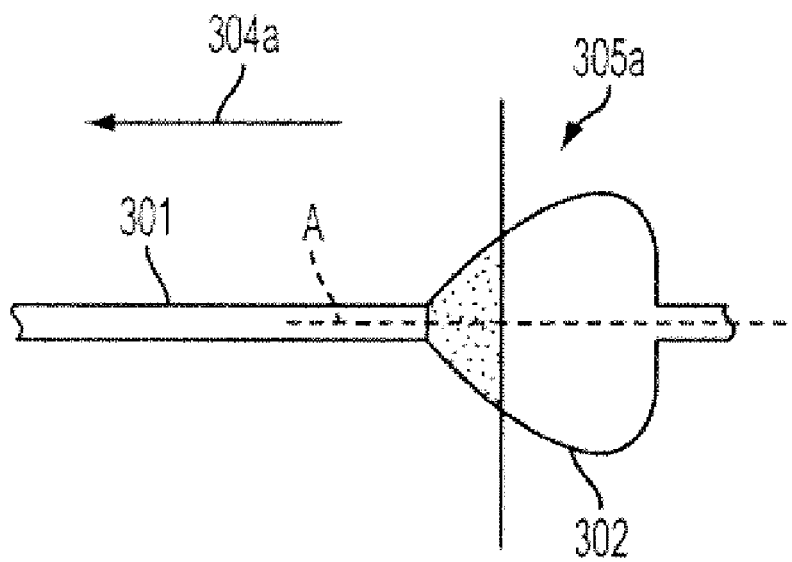
FIG. 3B depicts an inflated tulip-shaped balloon catheter in a various stage of use in accordance with an embodiment of the present subject matter.

Another embodiment of the present subject matter provides a method of using the balloon catheter to perform a pericardiotomy on a subject. The method comprises: providing a balloon catheter as described herein; advancing the balloon catheter into the pericardial space; inflating the balloon; pulling the inflated balloon catheter back through the pericardium to slowly increase the size of the hole in the pericardium. For example, as seen in FIG. 3A, the inflated tulip-shaped balloon catheter comprising a catheter 301 and an inflated tulip-shaped balloon 302 is pulled 304 through the pericardium 305 where a small hole was made in the pericardium by the initial insertion of the catheter. FIG. 3B depicts the inflated tulip-shaped balloon catheter comprising a catheter 301 and an inflated tulip-shaped balloon 302 pulled further 304a through the pericardium 305a where the size of the hole in the pericardium is increased. The catheter may be pulled until the entire inflated balloon is pulled out of the pericardial space to create the pericardial window. Alternatively, the catheter may be pulled until the desired size of the pericardial window is created, but prior to the entire inflated balloon being removed from the pericardial space. The method may further comprise deflating the balloon prior to removing the balloon from the subject. The method may also further comprise using ultrasound to verify that the balloon catheter is in the pericardial space.

In embodiments wherein the balloon catheter comprises a second balloon, the method may further comprise inflating the second balloon to secure and prevent the catheter from being pulled out of the pericardial space. The second balloon may be deflated prior to removal from the subject.

The balloon catheter of the present subject matter may also be used for balloon atrial septostomy, also known as the Rashkind procedure. Balloon atrial septostomy is a catheter-based procedure that widens the atrial septal defect ("ASD"), which is a hole between the two upper chambers of the heart. The procedure is performed on an infant as a temporary solution to improve circulation until the underlying cardiac defect can be repaired. The method comprises advancing the balloon catheter through the ASD; inflating the balloon and pulling the balloon catheter back through the septal defect to widen the ASD. Widening the ASD allows oxygen-rich and oxygen-poor blood to mix and improve the availability and circulation of oxygen-rich blood until the underlying heart defect can be surgically repaired.

The present subject matter is also directed to a kit for withdrawing fluid from the pericardial space by pericardiocentesis for evaluation of the fluid for diagnostic purposes or to remove the excess fluid causing compression of the heart and a kit for pericardiotomy. The kit is an assemblage of materials or components, including at least one of the inventive balloon catheters. The exact nature of the components configured in the inventive kit depends on its intended purpose. For example, some embodiments are configured for the purpose of performing pericardiocentesis. In other embodiments, the kits are configured particularly for the purpose of performing percutaneous pericardiotomy. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to perform pericardiocentesis or to perform a percutaneous pericardiotomy. Optionally, the kit also contains other useful components, such as, one or more needles, scalpels, alligator clips, ECG connector wires, three-way stop cock with lock nut, guide wires, drainage bags, syringes, local anesthetics (e.g., lidocaine), disinfectants (e.g., iodine), sutures, gauze, bandaging materials or other useful paraphernalia as will be readily recognized by those of skill in the art.

The materials or components assembled in the kit can be provided to the practitioner stored in any convenient and suitable ways that preserve their operability and utility. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit may be those customarily utilized in pericardiocentesis kits. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

Various embodiments of the subject matter are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the subject matter known to the applicant at this time of filing the application has been presented and is intended for the purposes of illustration and description. The present description is not intended to be exhaustive nor limit the subject matter to the precise form disclosed and many modifications and variations are possible in the light of the above teachings. The embodiments described serve to explain the principles of the subject matter and its practical application and to enable others skilled in the art to utilize the subject matter in various embodiments and with various modifications as are suited to the particular use contemplated. Therefore, it is intended that the subject matter not be limited to the particular embodiments disclosed for carrying out the subject matter.

While particular embodiments of the present subject matter have been shown and described, it will be obvious to those skilled in the art that, based upon the teachings herein, changes and modifications may be made without departing from this subject matter and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. An apparatus, comprising:
   a catheter;
   a first inflatable balloon attached to the catheter,
      wherein the first inflatable balloon is not at or near the distal end of the catheter, and
      wherein the first inflatable balloon is a tulip-shaped balloon that has an axis and comprises a first section proximal to the user being generally conical along the axis, and a second section distal to the user being generally half-spherical along the axis, and
   a second inflatable balloon attached to the catheter and distal to the first inflatable balloon,
      wherein the second inflatable balloon is not at or near the distal end of the catheter.

2. The apparatus according to claim 1, wherein the length of the first section is shorter than the length of the second section.

3. The apparatus according to claim 1, wherein the length of the first section is longer than the length of the second section.

4. The apparatus according to claim 1, wherein the length of the first section is substantially equal to the length of the second section.

5. The apparatus according to claim 1, wherein the inflatable tulip-shaped balloon has a diameter of 5 to 30 mm when fully inflated and a length of 5 to 30 mm when fully inflated.

6. The apparatus according to claim 1, wherein the catheter size ranges from 5 to 15 French.

7. The apparatus according to claim 1, further comprising at least one drainage hole in the catheter.

8. The apparatus according to claim 1, wherein the catheter is a pigtail catheter or a straight catheter.

9. The apparatus according to claim 1, wherein the second inflatable balloon is disk-shaped or spherical.

10. The apparatus according to claim 1, wherein the second inflatable balloon has a maximum inflated diameter smaller than the maximum diameter of the first inflatable balloon, when inflated.

11. The apparatus according to claim 1, wherein the first inflatable balloon and second inflatable balloon are each composed of a material independently selected from the group consisting of polyvinyl chloride, polyethylene terephthalate, nylon, rubber, polyethylene and polyurethane.

12. The apparatus according to claim 1, further comprising at least one lumen in communication with the catheter for inflation and/or deflation of the first inflatable balloon and/or the second inflatable balloon.

13. The apparatus according to claim 1, further comprising a syringe affixed to the catheter for inflation and/or deflation of the first inflatable balloon and/or the second inflatable balloon.

14. The apparatus according to claim 1, further comprising a stop-cock affixed to the catheter for sealing the first inflatable balloon and/or the second inflatable balloon.

15. The apparatus according to claim 1, further comprising a guidewire for placement of the apparatus during operation.

16. The apparatus according to claim 1, further comprising an ultrasound for viewing of the apparatus during operation.

17. The apparatus according to claim 1, wherein the catheter is a braided catheter.

18. A method, comprising:
   providing an apparatus, comprising:
   a catheter, and
   a first inflatable balloon attached to the catheter,
      wherein the first inflatable balloon is not at or near the distal end of the catheter, and
      wherein the first inflatable balloon is a tulip-shaped balloon that has an axis and comprises a first section proximal to the user being generally conical along the axis, and a second section distal to the user being generally half-spherical along the axis, and
   a second inflatable balloon attached to the catheter and distal to the first inflatable balloon,
      wherein the second inflatable balloon is not at or near the distal end of the catheter;
   advancing the apparatus into a pericardial space;
   inflating the first balloon to encompass the pericardial space; and
   draining the fluid from the pericardial space.

19. The method according to claim 18, wherein the apparatus further comprises a ultrasound device for viewing catheter placement.

20. The method according to claim 18, further comprising pulling the inflated first inflatable balloon and catheter through the pericardium to enlarge the pericardial space, prior to draining the fluid.

21. The method according to claim 18, further comprising deflating the first inflatable balloon and removing the apparatus from the pericardial space, prior to draining the fluid.

22. The method according to claim 18, wherein the catheter is a pigtail catheter or a straight catheter.

23. A method according to claim 18, further comprising inflating the second inflatable balloon to secure and prevent the catheter from being pulled out of the pericardial space, prior to draining the fluid.

24. The method according to claim 18, further comprising pulling the first inflatable balloon back towards the pericardium to enlarge the pericardial space, prior to draining the fluid.

25. The method according to claim 18, further comprising deflating the first inflatable balloon and second inflatable balloon, and removing the apparatus from the pericardial space, prior to draining the fluid.

26. The method according to claim 18, wherein the catheter is a braided catheter.

27. A kit for pericardiocentesis comprising:
   a catheter for draining the pericardial space;
   a first inflatable balloon attached to the catheter, for enlarging the pericardial space, wherein the first inflatable balloon is not at or near the distal end of the catheter, and wherein the first inflatable balloon is a tulip-shaped balloon that has an axis and comprises a first section proximal to the user being generally conical along the axis, and a second section distal to the user being generally half-spherical along the axis, and a second inflatable balloon attached to the catheter and distal to the first inflatable balloon, for securing the catheter, wherein the second inflatable balloon is not at or near the distal end of the catheter.

\* \* \* \* \*